United States Patent
Rodriguez Bravo et al.

(10) Patent No.: US 11,724,486 B2
(45) Date of Patent: Aug. 15, 2023

(54) PRINTING CUSTOMIZED MEDICATION BASED ON CURRENT USER DATA AND MEDICAL RECORDS OF THE USER

(71) Applicant: Kyndryl, Inc., New York, NY (US)

(72) Inventors: Cesar Augusto Rodriguez Bravo, Alajuela (CR); Sarbajit K. Rakshit, Kolkata (IN); Shikhar Kwatra, Durham, NC (US); Jeremy R. Fox, Georgetown, TX (US)

(73) Assignee: Kyndryl, Inc., New York, NY (US)

( * ) Notice: Subject to any disclaimer, the term of this patent is extended or adjusted under 35 U.S.C. 154(b) by 922 days.

(21) Appl. No.: 16/506,178

(22) Filed: Jul. 9, 2019

(65) Prior Publication Data

US 2021/0008869 A1   Jan. 14, 2021

(51) Int. Cl.
| | | |
|---|---|---|
| *B41F 17/36* | (2006.01) | |
| *A61K 9/24* | (2006.01) | |
| *G16H 10/60* | (2018.01) | |
| *G16H 20/10* | (2018.01) | |
| *H04L 67/12* | (2022.01) | |
| *B33Y 50/00* | (2015.01) | |
| *A61M 5/172* | (2006.01) | |

(Continued)

(52) U.S. Cl.
CPC .............. *B41F 17/36* (2013.01); *A61K 9/209* (2013.01); *A61M 5/1723* (2013.01); *B33Y 50/00* (2014.12); *G16H 10/60* (2018.01); *G16H 20/10* (2018.01); *G16H 70/40* (2018.01); *H04L 67/12* (2013.01); *A61J 3/007* (2013.01); *B33Y 10/00* (2014.12); *B33Y 70/00* (2014.12); *B33Y 80/00* (2014.12)

(58) Field of Classification Search
CPC ......... B41F 17/36; B33Y 50/00; G16H 10/60; G16H 70/40; G16H 20/10; A61M 5/1723; A61K 9/209; H04L 67/12
See application file for complete search history.

(56) References Cited

U.S. PATENT DOCUMENTS

| | | |
|---|---|---|
| 5,490,962 A | 2/1996 | Cima |
| 5,518,680 A | 5/1996 | Cima |

(Continued)

FOREIGN PATENT DOCUMENTS

| | | | | |
|---|---|---|---|---|
| CA | 2568542 A1 * | 8/2005 | ............... | A61K 9/14 |
| CA | 2809966 A1 * | 4/2012 | ............. | A61K 31/16 |

(Continued)

OTHER PUBLICATIONS

Ciccatelli, "Government and 3D Printing: A New Line of Innovation to Protect", IPWatchdog, Nov. 16, 2017, available at IPwatchdog.com (retrieved Sep. 29, 2022) (Year: 2017).*

(Continued)

*Primary Examiner* — Scott C Anderson
(74) *Attorney, Agent, or Firm* — Erik Swanson; George S. Blasiak; Heslin Rothernberg Farlye & Mesiti P.C.

(57) ABSTRACT

A computer-implemented method for printing customized 3D medication based on the current user data and one or more medical records of the user. The method obtains current user data via one or more user IoT sensors and accesses one or more medical records of the user. The method further determines a medication design based on the obtained current user data and the accessed one or more medical records of the user and prints a 3D medication based on the determined medication design.

20 Claims, 5 Drawing Sheets

(51) Int. Cl.
*G16H 70/40* (2018.01)
*A61J 3/00* (2006.01)
*B33Y 80/00* (2015.01)
*B33Y 10/00* (2015.01)
*B33Y 70/00* (2020.01)

(56) References Cited

U.S. PATENT DOCUMENTS

| | | | |
|---|---|---|---|
| 5,869,170 | A | 2/1999 | Cima |
| 2002/0015728 | A1 | 2/2002 | Payumo |
| 2003/0198677 | A1 | 10/2003 | Pryce Lewis |
| 2004/0005360 | A1 | 1/2004 | Wang |
| 2006/0003005 | A1 | 1/2006 | Cao |
| 2009/0306633 | A1 | 12/2009 | Trovato |
| 2013/0310664 | A1 | 11/2013 | Kozloski |
| 2016/0256240 | A1* | 9/2016 | Shivapuja .......... A61C 13/0013 |
| 2017/0027168 | A1* | 2/2017 | Heath .................. A61P 17/00 |
| 2017/0185745 | A1* | 6/2017 | Wartski ............... G16H 20/13 |
| 2018/0147776 | A1* | 5/2018 | Kotani ................. B33Y 70/00 |
| 2018/0281284 | A1* | 10/2018 | Elgar ................... B29C 31/085 |
| 2020/0086553 | A1* | 3/2020 | Mojdeh ................ B29C 64/236 |

FOREIGN PATENT DOCUMENTS

| | | | | |
|---|---|---|---|---|
| CN | 105534713 | A | | 5/2016 |
| CN | 106109245 | A | | 11/2016 |
| CN | 106113513 | A | | 2/2018 |
| KR | 20150078774 | A | | 7/2015 |
| WO | WO-2009022821 | A2 | * | 2/2009 ............ A61K 31/35 |

OTHER PUBLICATIONS

Aprecia, "The World's First 3DP Dosage Form", https://www.aprecia.com/technology/zipdose, printed Jun. 29, 2019, pp. 1-5.

Dexcom, "The Dexcom G6 Continuous Glucose Monitoring (CGM) System", printed Jun. 29, 2019, pp. 1-4.

https://www.wearable-technologies.com/2018/05/innovative-bracelet-wi . . . , "Innovative Bracelet Will Monitor Your Blood Pressure 24 Hours a Day", printed Jun. 29, 2019, pp. 1-2.

Huang et al., "3D Printing Drugs: More Precise, More Personalized", published in Pharma Times Magazine, Jan. 2018, http://www.pharmatimes.com/magazine/2018/janfeb/3d_printing_drugs . . . , pp. 1-4.

Kite_Powell, "FDA Approved 3D Printed Drug Available in the US", https://www.forbes.com/sites/ienniferhicks/2016/03/22/fda-approved-3d- . . . , Mar. 22, 2016, pp. 1-3.

Mell et al., "The NIST Definition of Cloud Computing", National Institute of Standards and Technology, Special Publication 800-145, Sep. 2011, pp. 1-7.

Reads, "The Big Ideas 3D-Printing Brings to Big Pharma", Huffington Post, Dec. 14, 2018, pp. 1-3.

S. Salar-Behzadi et al., "Gluing Pills Technology for the Production of Multi-Layer Tablets." Pharmaceutical Technology, 2017 Supplement, Apr. 1, 2017 [Accessed May 3, 2019], http://www.pharmtech.com/gluing-pills-technology-production-multi-layer-tablets.

Salar-Behzadi et al., Gluing Pills Technology for the Productiofn of Multi-Layer Tablets, PharmTech.com, Apr. 1, 2017, pp. 1-7.

Shende, "Integration of 3D printing with dosage forms: A new perspective for modern healthcare," Biomedicine & Pharmacotherapy, vol. 107, 2018, pp. 146-154.

Vandrico Inc., "Zephyr BioModule", Body Location, printed Jun. 30, 2019, pp. 1-4.

www.3ders.org, "DrugPrinter, print any drug instantly?", Apr. 23, 2014, pp. 1-11.

* cited by examiner

PRINTING CUSTOMIZED MEDICATION BASED ON CURRENT USER DATA AND MEDICAL RECORDS OF THE USER

BACKGROUND

The present invention relates generally to the field of cognitive computing and more particularly to data processing for three-dimensional (3D) printing of customized medication designs.

3D printing technology is a technique that is revolutionizing the medication production industry. 3D printing can consolidate multiple medicines into a single medication by printing layer by layer and is further capable of printing a medication that can release each medicine into a patient at a targeted time based on an easily adjustable medication design.

BRIEF SUMMARY

Embodiments of the present invention disclose a method, a computer program product, and a system.

According to an embodiment, a method, in a data processing system including a processor and a memory, for implementing a program. The method obtains current user data via one or more user Internet of Things (IoT) sensors and accesses one or more medical records of the user. The method further determines a medication design based on the obtained current user data and the accessed one or more medical records of the user and prints a 3D medication based on the determined medication design.

According to another embodiment, a computer program product for directing a computer processor to implement a program. The storage device embodies program code that is executable by a processor of a computer to perform a method. The method obtains current user data via one or more user IoT sensors and accesses one or more medical records of the user. The method further determines a medication design based on the obtained current user data and the accessed one or more medical records of the user and prints a 3D medication based on the determined medication design.

According to another embodiment, a system for implementing a program that manages a device, includes one or more computer devices each having one or more processors and one or more tangible storage devices. The one or more storage devices embody a program. The program has a set of program instructions for execution by the one or more processors. The method obtains current user data via one or more user IoT sensors and accesses one or more medical records of the user. The method further determines a medication design based on the obtained current user data and the accessed one or more medical records of the user and prints a 3D medication based on the determined medication design.

DETAILED DESCRIPTION

Medication production processes have transformed over the years. Medication production processes have shifted from compounding medications to printing medications using 3D printers. 3D printers are being used extensively in manufacturing to print medications and will be readily used by consumers and retailers to print medications in the near future. 3D printers print each medication (e.g., capsules, tablets, pills, etc.) layer by layer, wherein each layer comprises a medicine or a dissolvable filler material. However, current 3D printing technology is limited because it does not consider all relevant data to effectively customize each medication specific to each user.

For example, a user goes to a pharmacist with a doctor's prescription to get a medication. Current 3D printers allow pharmacists to print medications based on the doctor's prescription. However, current technology considers limited data, such as doctor's prescription and allergies of the user. One of the issues that the present invention seeks to resolve is to create a customized medication design for a customized treatment. The present invention may do this by printing a 3D medication based on a determined optimal medication design. The Optimal medication design is determined based on obtained current user data via user's IoT sensors and accessed medical records of the user.

Throughout the present invention disclosure, reference to a capsule type medication (e.g., capsules, tablets, pills, etc.) is not limiting but rather may further include any solid type medications, any powder type medications, any liquid type medications, or any other type of medications known to one of ordinary skill in art.

Throughout the present invention disclosure, reference to a 3D printer is not limiting but rather may further include any spraying devices, any manufacturing devices, or any other type of devices capable of making medications known to one of ordinary skill in art.

Throughout the present invention disclosure, reference to printing is not limiting but may further include spraying, melting, molding, or any other method of creating medications known to one of ordinary skill in art.

A medicine for purposes of the present invention, is a chemical composition of at least one chemical.

A medication for purposes of the present invention, is a combination of one or more medicines within a medication design. A medication design for purposes of the present invention, includes how a medication is packaged (e.g., capsule, tablet, pill, etc.).

Hereinafter, exemplary embodiments of the present invention will be described in detail with reference to the attached drawings.

The present invention is not limited to the exemplary embodiments below but may be implemented with the various modifications within the scope of the present invention. In addition, the drawings used herein are for purposes of illustration, and may not show actual dimensions.

Figure 1:
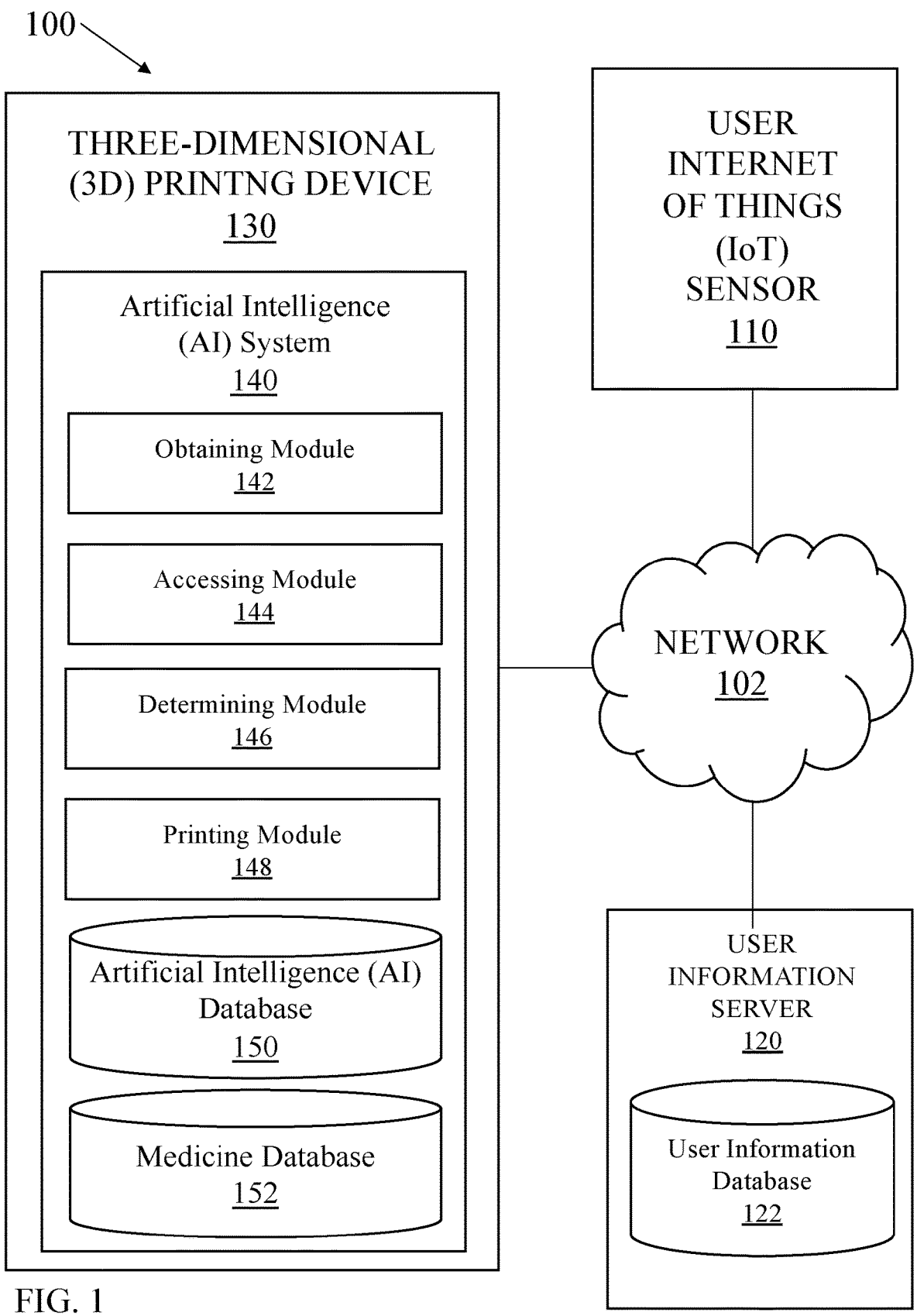
FIG. 1 illustrates an artificial intelligence (AI) computing environment, in accordance with an embodiment of the present invention.

FIG. 1 illustrates AI computing environment 100, in accordance with an embodiment of the present invention. AI computing environment 100 includes user IoT sensor 110, user information server 120, and 3D printing device 130 all connected via network 102. The setup in FIG. 1 represents an example embodiment configuration for the present invention and is not limited to the depicted setup in order to derive benefit from the present invention.

With reference to FIG. 1, user IoT sensor 110 may be a wearable device, mobile device, laptop computer, tablet computer, netbook computer, personal computer (PC), a desktop computer, a personal digital assistant (PDA), a smart phone, or any programmable electronic device capable of communicating with user information server 120 and 3D printing device 130 via network 102. User IoT sensor 110 may include internal and external hardware components, as depicted and described in further detail below with reference to FIG. 3. In other embodiments, user IoT sensor 110 may be implemented in a cloud computing environment, as described in relation to FIGS. 4 and 5, herein. User IoT sensor 110 may also have wireless connectivity capabilities allowing it to communicate with user information server 120, 3D printing device 130, and other devices or servers over network 102.

In exemplary embodiments, user IoT sensor 110 may include an embedded computing program or device, or a separate computing program or device, that allows data to be transmitted to a server, such as user information server 120, or a device, such as 3D printing device 130, across network infrastructure, such as network 102. For example, user IoT sensor 110 may be capable of transmitting a user identifier, food consumption data of the user, heart rate of the user, respiration rate of the user, blood pressure of the user, blood sugar level of the user, body temperature of the user, medication consumption data of the user, sleep pattern data of the user, or any other information known to one of ordinary skill in the art. User IoT sensor 110 may transfer information periodically to a server, such as user information server 120, or a device, 3D printing device 130, where this information may get stored.

In exemplary embodiments, users may configure which data may be transmitted and/or stored on a server (e.g., user information server 120) or on a device (e.g., 3D printing device 130) via IoT devices (e.g., user IoT sensor 110). In exemplary embodiments, users provide consent and are provided with full disclosure before any user data gets obtained, stored, accessed and/or transmitted. Users can opt-in or opt-out of sharing user data at any time.

In various embodiments, user IoT sensor 110 is capable of being embedded with various devices (e.g., 3D printing device 130) that contain a computer processing unit (CPU), memory, and power source, and may be capable of communicating with user information server 120 and 3D printing device 130 over network 102.

With continued reference to FIG. 1, user information server 120 includes user information database 122. In various embodiments, user information server 120 may be a laptop computer, tablet computer, netbook computer, personal computer (PC), a desktop computer, a personal digital assistant (PDA), a smart phone, or any programmable electronic device capable of communicating with user IoT sensor 110 and 3D printing device 130 via network 102. While user information server 120 is shown as a single device, in other embodiments, user information server 120 may be comprised of a cluster or plurality of computing devices, working together or working separately.

In an exemplary embodiment, user information database 122 may store user data as one or more data objects. The user data may include current disease status of the user, disease history of the user, psychological history of the user, medical history of the user, current medication prescriptions of the user, medication prescription history of the user, doctor recommendations, doctor comments, preferred medication delivery method of the user, maximum physical size of medication the user can consume, or any other category or information known to one of ordinary skill in the art. User information database 122 is capable of being dynamically updated. In exemplary embodiments, users provide consent and are provided with full disclosure before any user data gets obtained, accessed, stored, and/or transmitted. Users can opt-in or opt-out of sharing user data at any time.

In exemplary embodiments, user information database 122 may receive input from user IoT sensor 110.

In various embodiments, user information database 122 is capable of being stored on user IoT sensor 110, 3D printing device 130, AI system 140, or any other server or device connected to network 102, as a separate database.

Figure 3:
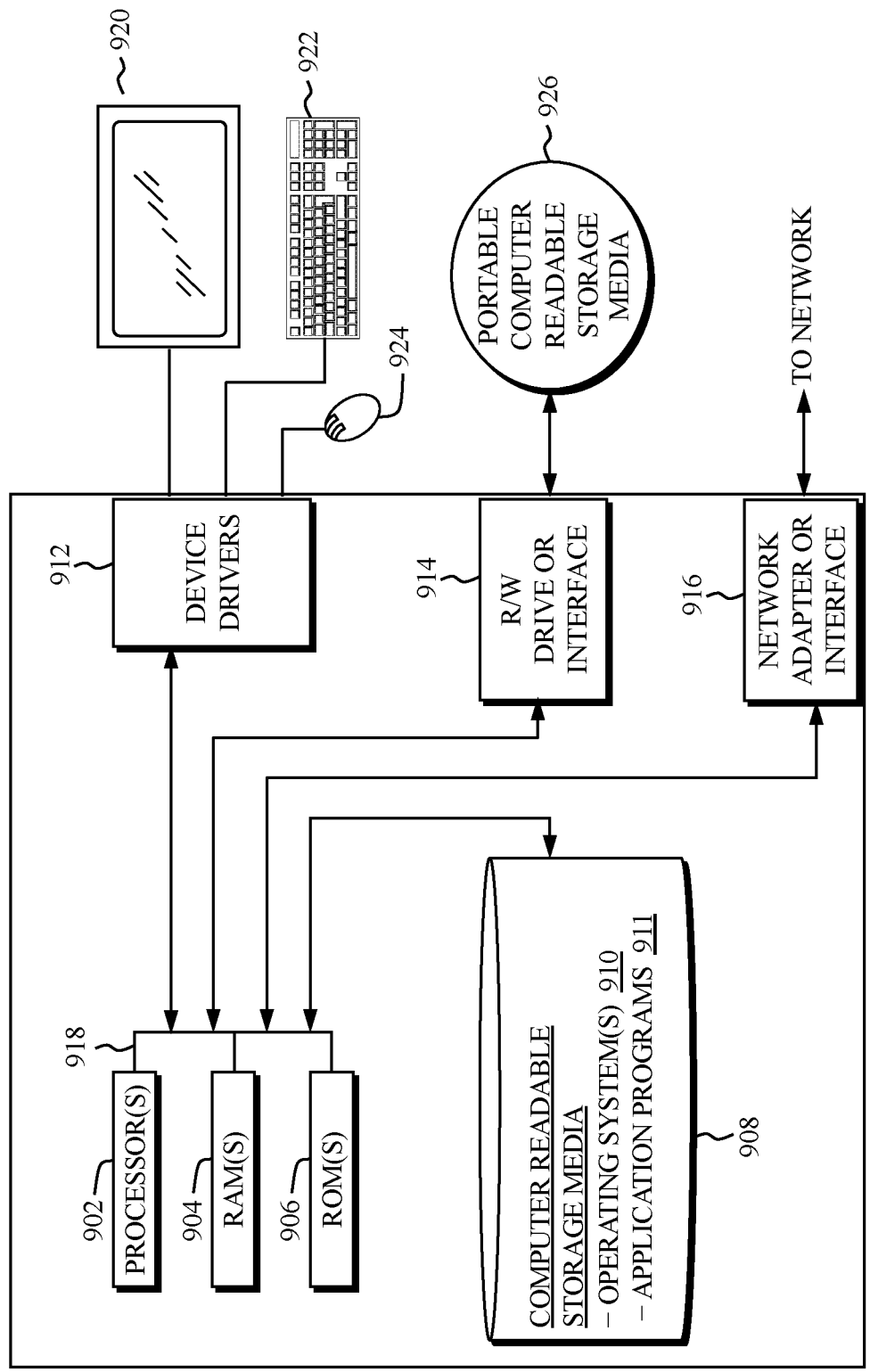
FIG. 3 is a diagram graphically illustrating the hardware components of the AI computing environment of FIG. 1, in accordance with an embodiment of the present invention.

With continued reference to FIG. 1, 3D printing device 130 includes AI system 140 and may be a laptop computer, tablet computer, netbook computer, personal computer (PC), a desktop computer, a personal digital assistant (PDA), a smart phone, or any programmable electronic device capable of communicating with user IoT sensor 110 and user information server 120 via network 102. 3D printing device 130 may include internal and external hardware components, as depicted and described in further detail below with reference to FIG. 3. In other embodiments, 3D printing device 130 may be implemented in a cloud computing environment, as described in relation to FIGS. 4 and 5, herein. 3D printing device 130 may also have wireless connectivity capabilities allowing it to communicate with user IoT sensor 110, user information server 120, and other devices or servers over network 102.

In exemplary embodiments, AI system 140 may obtain current user data via user IoT sensor 110, and one or more medical records of the user from user information database 122.

In exemplary embodiments, AI system 140 may be a computer program on 3D printing device 130 that includes AI database 150, medicine database 152, and instruction sets, executable by a processor. The instruction sets may be described using a set of functional modules. AI system 140 receives input from user IoT sensor 110, user information server 120. In alternative embodiments, AI system 140 may be a computer application on a separate electronic device, such as user IoT sensor 110, or on a separate server, such as user information server 120.

In an exemplary embodiment, AI database 150 may store learned interactions of a user with one or more medicines based on a plurality of physiological states of the user, medication designs, a user identifier, gastric fluid properties history of the user, or any other category or information known to one of ordinary skill in the art.

Physiology is how organisms, organ systems, organs, cells, and biomolecules carry out the chemical and physical functions that exist in a living system. Physiological states of a user may include the condition or state of the body or bodily functions on a cellular level. For example, when a user is hungry, the gastric fluid in the user's stomach may have higher acidity levels; or when a user is tired, the neuronal activity of the user's neural network is slower.

AI database 150 is capable of being dynamically updated. In exemplary embodiments, users provide consent and are provided with full disclosure before any user interaction data gets stored. Users can opt-in or opt-out of sharing user interaction data at any time.

In exemplary embodiments, the learned interactions of a user with one or more medicines based on a plurality of physiological states of the user may include: dissolution rate of one or more medicine in relation to gastric fluid properties of the user; psychological effects the user experienced after taking one or more medicines (e.g., depression, anger, etc.), physical effects the user experienced after taking one or more medicines (e.g., migraines, drowsiness, rashes, allergic reaction, etc.), or any other category or information known to one of ordinary skill in the art.

In exemplary embodiments, AI database 150 may store information, for example, as a data object with the following information: A user identifier (e.g., A0001), gastric fluid properties history of the user (e.g., without meal consumption: pH of 2; immediately after meal consumption: pH of 4), medication design (e.g., medicine "X" design file), dissolution rate of one or more medicines in relation to gastric fluid properties of the user (e.g., dissolution rate of medicine "Y" with a 50% concentration rate is 4 mm per minute when the user did not consume any meal, and 2 mm per minute when the user took the medicine right after meal consumption), psychological effects the user experienced after taking one or more medicines (e.g., the user experienced slight depression after consuming medicine "Y"), physical effects the user experienced after taking one or more medicines (e.g., small rashes on the neck of the user after consuming medicine "Y"). As such, the user data object, in this case, may be stored in AI database 150 as <A0001; without meal consumption: pH of 2; immediately after meal consumption: pH of 4; medicine "X" design file; dissolution rate of medicine "Y" with 50% concentration rate is 4 mm per minute when the user did not consume any meal, and 2 mm per minute when the user took the medicine right after meal consumption; the user experienced slight depression after consuming medicine "Y"; small rashes on the neck of the user after consuming medicine "Y">.

In an exemplary embodiment, medicine database 152 may include data objects organized as a list of medicines, chemical properties of each medicine, replacement medicines (e.g., generics), recommended dosage of each medicine based on specific user, chemical interactions of each medicine with other medicines, or any other category or information known to one of ordinary skill in the art. Medicine database 152 is capable of being dynamically updated and may be represented in a table format. In exemplary embodiments, AI system 140 may be capable of accessing medicine database 152.

With continued reference to FIG. 1, the functional modules of AI system 140 include obtaining module 142, accessing module 144, determining module 146, and printing module 148.

Figure 2:
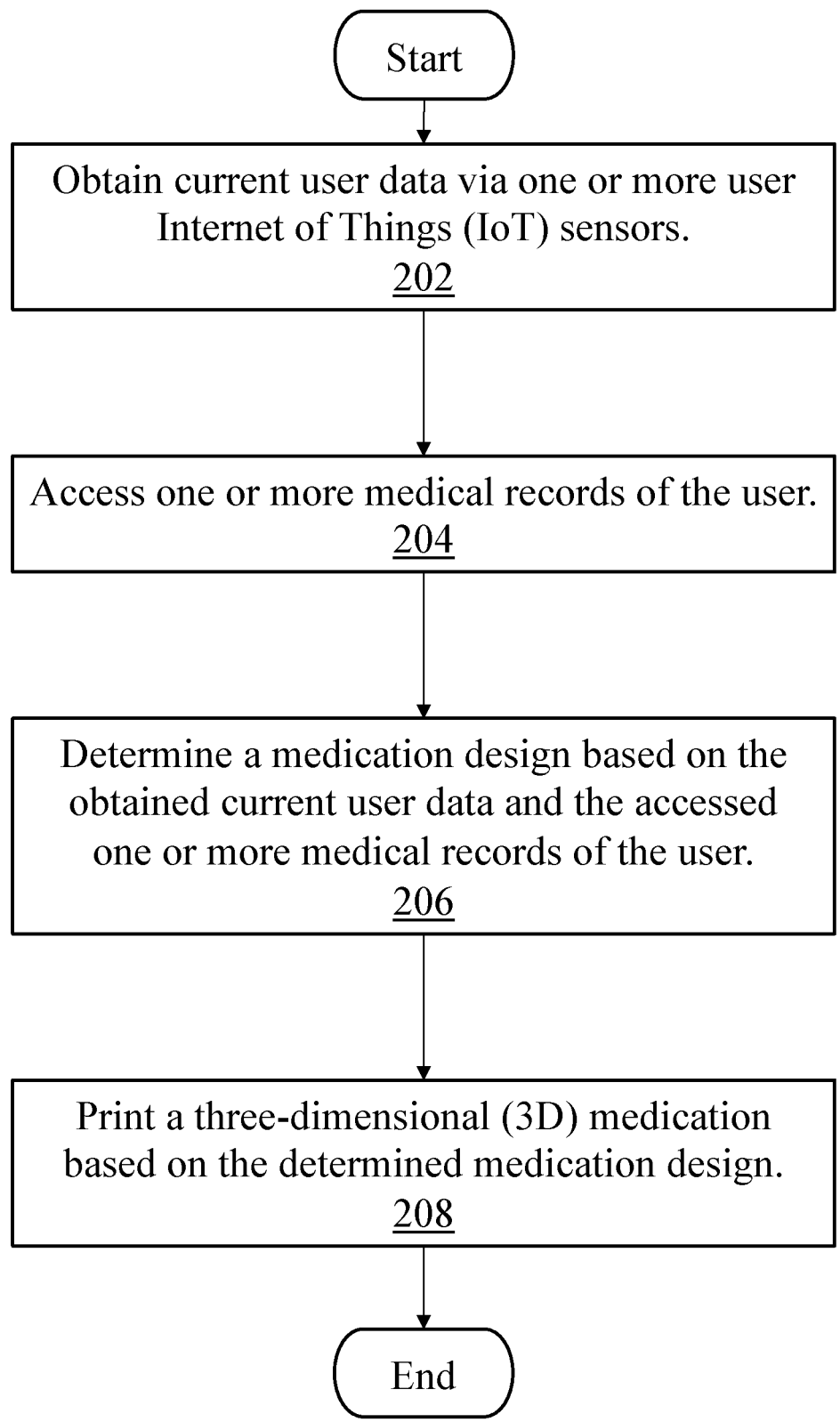
FIG. 2 is a flowchart illustrating the operation of an AI system of FIG. 1, in accordance with an embodiment of the present invention.

FIG. 2 is a flowchart illustrating the operation of AI system 140 of FIG. 1, in accordance with embodiments of the present invention.

With reference to FIGS. 1 and 2, obtaining module 142 includes a set of programming instructions, in AI system 140, to obtain current user data via one or more user IoT sensors (step 202). The set of programming instructions is executable by a processor.

In exemplary embodiments, obtaining module 142 obtains current user data that may include a user identifier, food consumption data of the user, heart rate of the user, respiration rate of the user, blood pressure of the user, blood sugar level of the user, body temperature of the user, medication consumption data of the user, sleep pattern data of the user, or any other information known to one of ordinary skill in the art. The obtained current user data is transmitted to AI system 140.

With reference to an illustrative example, John goes to a pharmacy to get his medication. A pharmacist enters John's prescription that John needs four medicines (e.g., medicine 1, 2, 3, and 4). Then, obtaining module 142 receives John's data from John's wearable IoT sensor 110, and John's mobile device. Obtained data is that John is vegetarian, he last consumed a meal within the last 2 hours, his heart rate is 100 beats per minute, his respiration rate is 15 breaths per minute, his blood pressure is 110 over 70, his blood sugar level is 80 mg/dL, his body temperature is 98.6° F., he last consumed 40 mg of medicine "A" 5 hours ago, and he slept for 6 hours last night.

With continued reference to FIGS. 1 and 2, accessing module 144 includes a set of programing instructions, in AI system 140, to access one or more medical records of the user (step 204). The set of programming instructions is executable by a processor.

In exemplary embodiments, accessing module 144 accesses medical records of the user that may include current disease status of the user, disease history of the user, psychological history of the user, medical history of the user, current medication prescriptions of the user, medication prescription history of the user, doctor recommendations, doctor comments, preferred medication delivery method of the user, maximum physical size of medication the user can consume, or any other category or information known to one of ordinary skill in the art. The accessed medical records of the user are transmitted to AI system 140.

With continued reference to the illustrative example above, accessing module 144 retrieves John's medical records from a user information server (e.g., John's primary physician's database). John's retrieved medical records indicate that he currently does not have any diseases, he had the flu 2 months ago, he has no record of impaired psychological history, he has a heart condition, he is currently taking medicine "A," past prescriptions include medicines "A," "B," "C," and "D," in past 6 months, his doctor recommends for an initial layer of the medication to be 1 mm for slower medicine application, he prefers medication in a capsule format, and he can only consume capsules smaller than 22 mm in length.

With continued reference to FIGS. 1 and 2, determining module 146 includes a set of programing instructions, in AI system 140, to determine a medication design based on the obtained current user data and the accessed one or more medical records of the user (step 206). The set of programming instructions is executable by a processor.

In exemplary embodiments, determined medication design comprises a dosage amount of one or more medicines, a thickness of one or more layers of dissolvable filler material placed between the one or more medicines, one or more dimensions of the medication, and any other relevant information to print a medication known to one of ordinary skill in the art.

In exemplary embodiments, the dissolvable filler material is a chemical composition of at least one chemical that dissolves when the filler material comes in contact with gastric fluid of a user. For example, filler material 1 and 2 are two different materials with different chemical compositions. Each filer material dissolves, when the filler material makes contact with gastric fluid of the user, at a different dissolution rate from one another.

In exemplary embodiments, a thickness of one or more layers of dissolvable filler material is important to meet a time gap requirement between the release of each of the one or more medicines within the medication. For example, if medicine 2 is instructed to be applied five minutes after the application of medicine 1, then the thickness of the dissolvable filler material 1 between medicine 1 and medicine 2 will be 5 mm, given that 1 mm of filler material 1 dissolves every minute.

In exemplary embodiments, the filler material may be comprised of various materials with varying dissolving rates. Based on the selected filler material and its associated dissolution rate, the thickness of the filler material, ultimately, changes.

In exemplary embodiments, the dosage amount includes the mass (e.g., milligrams), or any other determined dosage amount, of each of the one or more medicines that will be printed within the medication and the thickness of the layer of each of the one or more medicines.

In exemplary embodiments, each of the one or more layer comprises of one or more medicines or one or more filler materials. An order of one or more layers is important to meet the instructed order of medicine application. For example, medicine 2 needs to be applied after medicine 1. Thus, medicine 2 layer will be located farther in distance to the exterior of the medication in contrast to medicine 1 layer, which will be located closer in distance to the exterior of the medication than medicine 2 layer.

In exemplary embodiments, one or more dimensions are important to print a medication layer by layer to meet the medicine application workflow and the time gap between the release of each of the one or more medicines within the medication. Dimensions comprise shape and structure, length, width, and height. For example, the dimensions for hypothetical medication "A" may be 15 mm by 7 mm by 10 mm and medication "A" may be printed in an oval shape.

One or more dimensions may be one or more dimensions of the exterior of the medication and one or more dimensions of each of the one or more layers within the medication.

Determined medication design may be stored on AI database 150, user information database 122, or any other database connected to network 102.

In exemplary embodiments, determining module 146 is further capable of identifying medicine application work flow, wherein the medicine application work flow comprises an order of release of the one or more medicines within the medication, and a time gap between the release of each of the one or more medicines within the medication. Furthermore, determining module 146 determines the thickness of the one or more layers of the dissolvable filler material within the medication based on the identified time gap between the release of each of the one or more medicines within the medication.

In exemplary embodiments, medicine application work flow and time gap between the release of each one or more medicines within the medication are identified based on the accessed medical records of the user and data from a medicine database (e.g., medicine database 152). For example, based on a doctor's prescription and medical records of the user, determining module 146 identifies the medicine application workflow, that is medicine 2 is to be applied after applying medicine 1. Determining module 146 also identifies the time gap between the release of the one or more medicines within the medication. In this example, there should be a 5-minute gap after releasing medicine 1 and before releasing medicine 2, in order to prevent migraines.

In exemplary embodiments, determining module 146 is further capable of adjusting the determined medication design and the medicine application workflow based on the obtained current user data and learned interactions of the user with the one or more medicines based on a plurality of physiological states of the user. For example, if blood pressure level of the user is too low, determining module 146 adjusts the determined medication design to minimize the adverse effect of the medication by replacing one or more medicines that may further lower blood pressure with one or more recommended replacement medicine with the same medicinal effect that will not lower the blood pressure of the user. Recommended one or more replacement medicines may be determined by determining module 146 via lookup table from medicine database 152.

In exemplary embodiments, determining module 146 customizes the determined medication design to incorporate one or more user-inserted parameters. For example, if the user indicates that the user prefers to avoid medications with drowsy effects because the user needs to operate a vehicle, determining module 146 customizes the determined medication design. Determining module 146 customizes the determined medication design by replacing any medicine that may have a drowsy effect with a medicine that does not have a drowsy effect, if it exists, or at least replaces any medicine that may have a drowsy effect with a medicine that minimizes the drowsy effect of the determined medication.

In exemplary embodiments, determining module 146 is further capable of predicting gastric fluid properties of the user based on the learned interactions of the user with the one or more medicines and the plurality of physiological states of the user, recommending an optimal medication design and an optimal medicine application workflow based on the predicted gastric fluid properties of the user and adjusting the determined medication design based on the recommended optimal medication design and the recommended optimal medicine application workflow.

In exemplary embodiments, predicting gastric fluid properties of the user based on the learned interactions of the user with the one or more medicines and the plurality of physiological states of the user is important to determine a proper thickness of each of the one or more layers of the medication to meet the time gap between the release of each of the one or more medicines. For example, learned interactions of the user with one or more medicines and the plurality of physiological states of the user is that when the user has an empty stomach (e.g., has not eaten all day), filler 1 (i.e., located between medicine 1 and medicine 2) dissolves 2 minutes earlier than the identified time gap between medicine 1 and medicine 2. Thus, determining module 146 identifies that the gastric fluid of the user is more acidic than previously predicted because filler 1 dissolved faster than predicted, and learns that filler 1 should be thicker, when the user has an empty stomach, than previously determined to meet the determined time gap between medicine 1 and medicine 2. On the same note, when the user has a full stomach then filler 1 thickness is adjusted to account for the lower acidity levels of the gastric fluid in the user's stomach. In this fashion, the medication is tailored to a specific user based on current physiological states of the user and previously learned interactions.

In exemplary embodiments, an optimal medication design is important because such design is an adjusted medication design to a specific user. This customized medication design will be dynamically adjusted to meet the needs of the user and for a customized treatment.

In exemplary embodiments, gastric fluid properties for purposes of the present invention, may be an acidity of gastric fluid of the user and how long each of the one or more medicines and/or each of the one or more filler materials take to dissolve fully into the user when such medicine or material comes in contact with the gastric fluid of the user.

In exemplary embodiments, determining module 146 is further capable of predicting absorption rates of various medicines within the user, blood serum levels within the user, other diagnostic measures that are relevant to determine dosage levels of a medicine, optimal time for when the medicine ought to be consumed by the user, or any other variable information that is helpful in optimizing a medication design for a specific user.

With continued reference to the illustrative example above, the determined medicine application work flow and the time gap between the release of each of the one or more medicines within the medication design is as follows: medicines 1 and 2 are to be applied together, medicine 3 is to be applied 5 minutes after applying medicines 1 and 2 and medicine 4 is to be applied 3 minutes after applying medicine 3. Based on the time gap between the release of each of the one or more medicines, determined filler between combined medicine 1 and 2 and medicine 3 is 5 mm of filler 1 (i.e., dissolution rate of 1 mm per minute) and determined filler between medicine 3 and 4 is 6 mm of filler 2 (i.e., dissolution rate of 2 mm per minute). The determined medication design comprises that 50 milligrams of medicines 1, 2, 3, and 4 are included within the medication and each layer of the medicine is 2 mm in thickness. In addition, the determined medication design also indicates that 5 mm of filer 1, 6 mm of filler 2 and 1 mm of initial filler layer are to be included within the medication. It also includes information that dimensions of the medication are 18 mm by 10 mm by 5 mm in an oval capsule format.

With continued reference to FIGS. 1 and 2, printing module 148 includes a set of programing instructions, in AI system 140, to print a 3D medication based on the determined medication design (step 208). The set of programming instructions is executable by a processor.

In exemplary embodiments, printing module 148 creates the medication based on the determined medication design from determining module 146. For example, 3D printing device 130 will print one or more medications, layer by layer, based on the determined medication design.

In exemplary embodiments, multiple layers of the printed medication are dissolved, layer by layer, by a gastric fluid in a stomach of a user. Once any of multiple layers come into contact with the gastric fluid of the user, the contacted layer will start to dissolve gradually in accordance to the identified optimal medicine application workflow and the identified time gap between the release of each of the one or more medicines within the medication.

With continued reference to the illustrative example above, printing module 148 prints an encapsulated medication according to the determined medication design from determining module 146.

In an exemplary embodiment, network 102 is a communication channel capable of transferring data between connected devices and may be a telecommunications network used to facilitate telephone calls between two or more parties comprising a landline network, a wireless network, a closed network, a satellite network, or any combination thereof. In another embodiment, network 102 may be the Internet, representing a worldwide collection of networks and gateways to support communications between devices connected to the Internet. In this other embodiment, network 102 may include, for example, wired, wireless, or fiber optic connections which may be implemented as an intranet network, a local area network (LAN), a wide area network (WAN), or any combination thereof. In further embodiments, network 102 may be a Bluetooth network, a WiFi network, or a combination thereof. In general, network 102 can be any combination of connections and protocols that will support communications between user IoT sensor 110, user information server 120, and 3D printing device 130.

FIG. 3 is a block diagram depicting components of a computing device (such as user IoT sensor 110, user information server 120, or 3D printing device 130, as shown in FIG. 1), in accordance with an embodiment of the present invention. It should be appreciated that FIG. 3 provides only an illustration of one implementation and does not imply any limitations with regard to the environments in which different embodiments may be implemented. Many modifications to the depicted environment may be made.

Computing device of FIG. 3 may include one or more processors 902, one or more computer-readable RAMs 904, one or more computer-readable ROMs 906, one or more computer readable storage media 908, device drivers 912, read/write drive or interface 914, network adapter or interface 916, all interconnected over a communications fabric 918. Communications fabric 918 may be implemented with any architecture designed for passing data and/or control information between processors (such as microprocessors, communications and network processors, etc.), system memory, peripheral devices, and any other hardware components within a system.

One or more operating systems 910, and one or more application programs 911, such as AI system 140, may be stored on one or more of the computer readable storage media 908 for execution by one or more of the processors 902 via one or more of the respective RAMs 904 (which typically include cache memory). In the illustrated embodiment, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Computing device of FIG. 3 may also include a R/W drive or interface 914 to read from and write to one or more portable computer readable storage media 926. Application programs 911 on the computing device may be stored on one or more of the portable computer readable storage media 926, read via the respective R/W drive or interface 914 and loaded into the respective computer readable storage media 908.

Computing device of FIG. 3 may also include a network adapter or interface 916, such as a TCP/IP adapter card or wireless communication adapter (such as a 4G wireless communication adapter using OFDMA technology). Application programs 911 on the computing device may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may comprise copper wires, optical fibers, wireless transmission, routers, firewalls, switches, gateway computers and/or edge servers.

Computing device of FIG. 3 may also include a display screen 920, a keyboard or keypad 922, and a computer mouse or touchpad 924. Device drivers 912 interface to display screen 920 for imaging, to keyboard or keypad 922, to computer mouse or touchpad 924, and/or to display screen 920 for pressure sensing of alphanumeric character entry and user selections. The device drivers 912, R/W drive or interface 914 and network adapter or interface 916 may comprise hardware and software (stored on computer readable storage media 908 and/or ROM 906).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

It is to be understood that although this invention disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
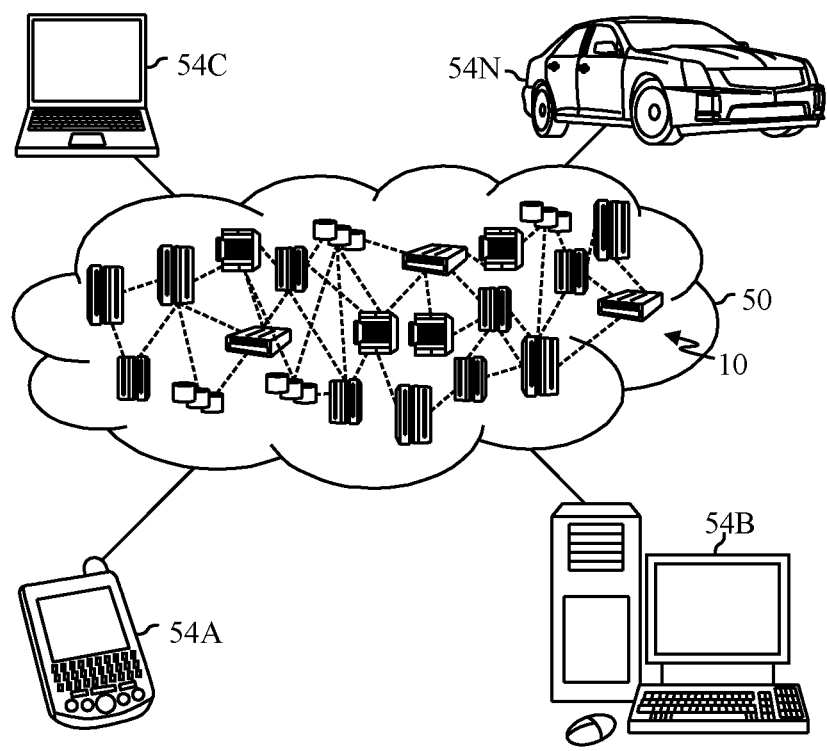
FIG. 4 depicts a cloud computing environment, in accordance with an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
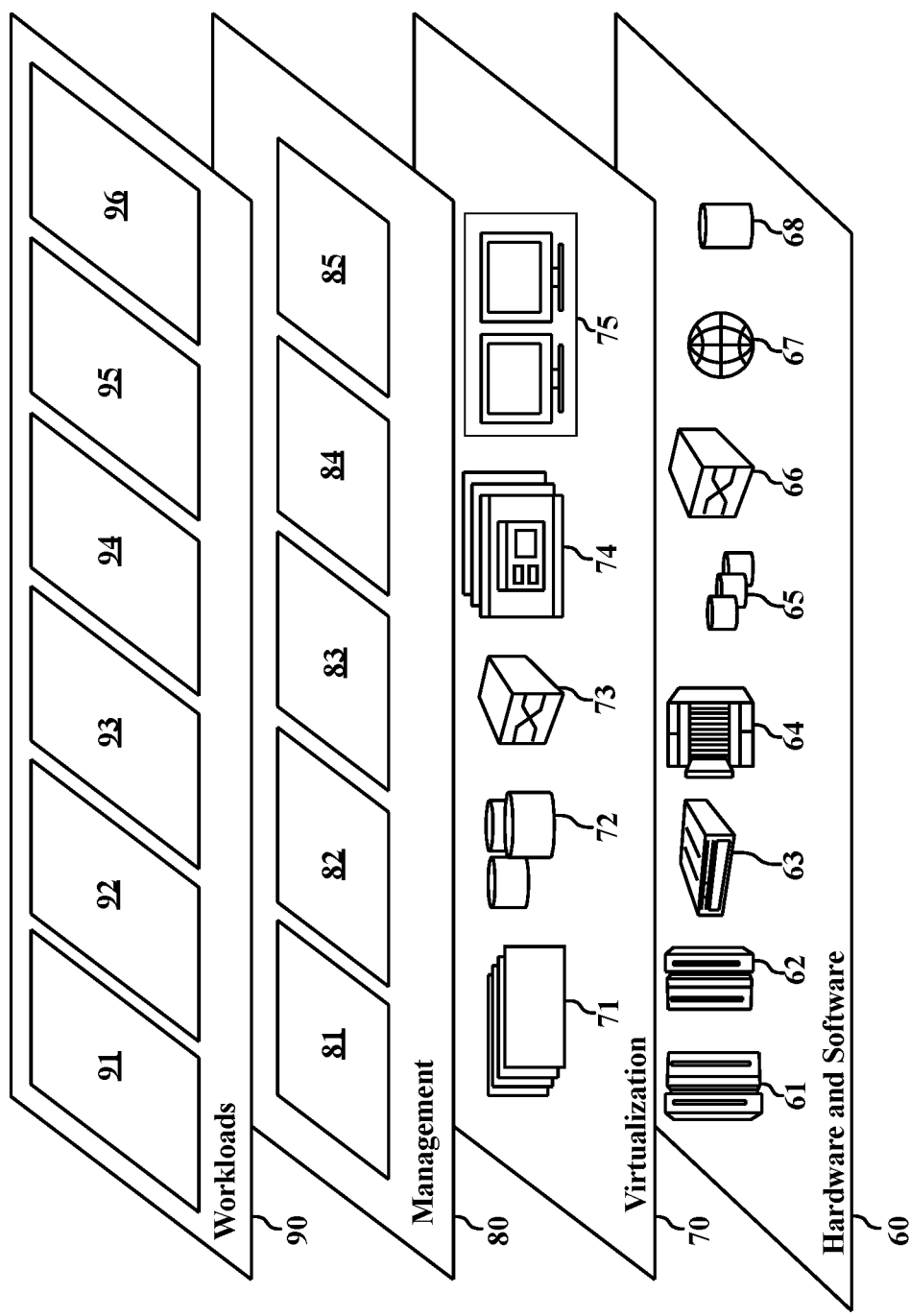
FIG. 5 depicts abstraction model layers of the illustrative cloud computing environment of FIG. 4, in accordance with an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and controlling access to data objects 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Based on the foregoing, a computer system, method, and computer program product have been disclosed. However, numerous modifications and substitutions can be made without deviating from the scope of the present invention. Therefore, the present invention has been disclosed by way of example and not limitation.

The invention claimed is:

1. A computer-implemented method comprising:
obtaining current user data via one or more user Internet of Things (IoT) sensors;
accessing one or more medical records of the user;
determining a medication design based on the obtained current user data and the accessed one or more medical records of the user, wherein the determined medication design comprises: a dosage amount of one or more medicines, a thickness of one or more layers of dissolvable filler material placed between the one or more medicines, and one or more dimensions of the medication; and
printing a three-dimensional (3D) medication based on the determined medication design.

2. The computer-implemented method of claim 1, wherein obtaining current user data via one or more IoT sensors comprises:
receiving at least one of the following in a group consisting of: a user identifier, food consumption data of the user, heart rate of the user, respiration rate of the user, blood pressure of the user, blood sugar level of the user, body temperature of the user, medication consumption data of the user, and sleep pattern data of the user.

3. The computer-implemented method of claim 1, wherein accessing one or more medical records of the user comprises:
retrieving at least one of the following in a group consisting of: current disease status of the user, disease history of the user, psychological history of the user, medical history of the user, current medication prescriptions of the user, medication prescription history of the user, doctor recommendations, doctor comments, preferred medication delivery method of the user, and maximum physical size of medication the user can consume.

4. The computer-implemented method of claim 1, wherein the determined medication design further comprises:
identifying medicine application work flow, wherein the medicine application work flow comprises an order of release of the one or more medicines within the medication, and a time gap between the release of each of the one or more medicines within the medication; and
determining the thickness of the one or more layers of the dissolvable filler material within the medication based on the identified time gap between the release of each of the one or more medicines within the medication.

5. The computer-implemented method of claim 4, further comprising:
adjusting the determined medication design and the medicine application workflow based on the obtained current user data; and
learning interactions of the user with the one or more medicines based on a plurality of physiological states of the user.

6. The computer-implemented method of claim 5, further comprising:
predicting gastric fluid properties of the user based on the learned interactions of the user with the one or more medicines and the plurality of physiological states of the user;
recommending an optimal medication design and an optimal medicine application workflow based on the predicted gastric fluid properties; and
adjusting the determined medication design based on the recommended optimal medication design and the recommended optimal medicine application workflow.

7. The computer-implemented method of claim 5, wherein adjusting the determined medication design and the medicine application workflow, further comprises:
customizing the determined medication design to incorporate one or more user-inserted parameters.

8. The computer-implemented method of claim 1, further comprising:
predicting gastric fluid properties of the user based on learned interactions of the user with one or more medicines of the medication design and a plurality of physiological states of the user;
recommending an optimal medication design and an optimal medicine application workflow based on the predicted gastric fluid properties; and
adjusting the determined medication design based on the recommended optimal medication design and the recommended optimal medicine application workflow.

9. The computer-implemented method of claim 1, wherein the determined medication design further comprises:
    identifying medicine application work flow, wherein the medicine application work flow comprises an order of release of the one or more medicines within the medication.

10. A computer program product for implementing a program that manages a device, the computer program product comprising a computer readable storage medium having program instructions embodied therewith, the program instruction executable by a processor of a computer to perform a method, the method comprising:
    obtaining current user data via one or more user Internet of Things (IoT) sensors;
    accessing one or more medical records of the user;
    determining a medication design based on the obtained current user data and the accessed one or more medical records of the user, wherein the determined medication design comprises: a dosage amount of one or more medicines, a thickness of one or more layers of dissolvable filler material placed between the one or more medicines, and one or more dimensions of the medication; and
    printing a three-dimensional (3D) medication based on the determined medication design.

11. The computer program product of claim 10, wherein obtaining current user data via one or more IoT sensors comprises:
    receiving at least one of the following in a group consisting of: a user identifier, food consumption data of the user, heart rate of the user, respiration rate of the user, blood pressure of the user, blood sugar level of the user, body temperature of the user, medication consumption data of the user, and sleep pattern data of the user.

12. The computer program product of claim 10, wherein accessing one or more medical records of the user comprises:
    retrieving at least one of the following in a group consisting of: current disease status of the user, disease history of the user, psychological history of the user, medical history of the user, current medication prescriptions of the user, medication prescription history of the user, doctor recommendations, doctor comments, preferred medication delivery method of the user, and maximum physical size of medication the user can consume.

13. The computer program product of claim 10, wherein the determined medication design further comprises:
    identifying medicine application work flow, wherein the medicine application work flow comprises an order of release of the one or more medicines within the medication, and a time gap between the release of each of the one or more medicines within the medication;
    determining the thickness of the one or more layers of the dissolvable filler material within the medication based on the identified time gap between the release of each of the one or more medicines within the medication;
    adjusting the determined medication design and the medicine application workflow based on the obtained current user data;
    learning interactions of the user with the one or more medicines based on a plurality of physiological states of the user;
    predicting gastric fluid properties of the user based on the learned interactions of the user with the one or more medicines and the plurality of physiological states of the user;
    recommending an optimal medication design and an optimal medicine application workflow based on the predicted gastric fluid properties; and
    adjusting the determined medication design based on the recommended optimal medication design and the recommended optimal medicine application workflow.

14. The computer program product of claim 13, wherein adjusting the determined medication design and the medicine application workflow, further comprises:
    customizing the determined medication design to incorporate one or more user-inserted parameters.

15. The computer program product of claim 10, wherein the determined medication design further comprises:
    identifying medicine application work flow, wherein the medicine application work flow comprises an order of release of the one or more medicines within the medication, and a time gap between the release of each of the one or more medicines within the medication.

16. A computer system for implementing a program that manages a device, comprising:
    one or more computer devices each having one or more processors and one or more tangible storage devices; and
    a program embodied on at least one of the one or more storage devices, the program having a plurality of program instructions for execution by the one or more processors, the program instructions comprising instructions for:
    obtaining current user data via one or more user Internet of Things (IoT) sensors;
    accessing one or more medical records of the user;
    determining a medication design based on the obtained current user data and the accessed one or more medical records of the user, wherein the determined medication design comprises: a dosage amount of one or more medicines, a thickness of one or more layers of dissolvable filler material placed between the one or more medicines, and one or more dimensions of the medication; and
    printing a three-dimensional (3D) medication based on the determined medication design.

17. The computer system of claim 16, wherein obtaining current user data from one or more IoT sensors comprises:
    receiving each of: a user identifier, food consumption data of the user, heart rate of the user, respiration rate of the user, blood pressure of the user, blood sugar level of the user, body temperature of the user, medication consumption data of the user, and sleep pattern data of the user.

18. The computer system of claim 16, wherein accessing one or more medical records of the user comprises:
    retrieving each of: current disease status of the user, disease history of the user, psychological history of the user, medical history of the user, current medication prescriptions of the user, medication prescription history of the user, doctor recommendations, doctor comments, preferred medication delivery method of the user, and maximum physical size of medication the user can consume.

19. The computer system of claim 16, wherein the determined medication design further comprises:
    identifying medicine application work flow, wherein the medicine application work flow comprises an order of release of the one or more medicines within the medication, and a time gap between the release of each of the one or more medicines within the medication;

determining the thickness of the one or more layers of the dissolvable filler material within the medication based on the identified time gap between the release of each of the one or more medicines within the medication;

adjusting the determined medication design and the medicine application workflow based on the obtained current user data;

learning interactions of the user with the one or more medicines based on a plurality of physiological states of the user;

predicting gastric fluid properties of the user based on the learned interactions of the user with the one or more medicines and the plurality of physiological states of the user;

recommending an optimal medication design and an optimal medicine application workflow based on the predicted gastric fluid properties; and adjusting the determined medication design based on the recommended optimal medication design and the recommended optimal medicine application workflow.

20. The computer system of claim 16, wherein the determined medication design further comprises:

identifying medicine application work flow, wherein the medicine application work flow comprises an order of release of the one or more medicines within the medication, and a time gap between the release of each of the one or more medicines within the medication.

* * * * *